US007255861B1

(12) United States Patent
Strominger et al.

(10) Patent No.: US 7,255,861 B1
(45) Date of Patent: *Aug. 14, 2007

(54) PREPARATIONS FOR INDUCING IMMUNOTOLERANCE AND USES THEREFOR

(75) Inventors: Jack L. Strominger, Lexington, MA (US); Kai W. Wucherpfennig, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/991,628

(22) Filed: Nov. 5, 1997

Related U.S. Application Data

(62) Division of application No. 08/400,796, filed on Mar. 7, 1995, now Pat. No. 5,874,531.

(51) Int. Cl.
*A61K 39/00* (2006.01)
*A61K 38/00* (2006.01)
*A61K 38/04* (2006.01)

(52) U.S. Cl. .................. 424/185.1; 514/14; 514/21

(58) Field of Classification Search ............ 424/185.1; 514/13
See application file for complete search history.

(56) References Cited

U.S. PATENT DOCUMENTS

| 5,130,297 A | 7/1992 | Sharma et al. |
| 5,194,425 A | 3/1993 | Sharma et al. |
| 5,874,531 A * | 2/1999 | Strominger et al. |
| 6,329,499 B1 * | 12/2001 | Ling et al. .................. 530/327 |

FOREIGN PATENT DOCUMENTS

| WO | WO 90/08161 | 7/1990 |
| WO | WO 92/16234 | 10/1992 |
| WO | WO 92/18150 | 10/1992 |
| WO | WO 93/10813 | 6/1993 |
| WO | WO 94/05303 | 3/1994 |
| WO | WO 94/06828 | 3/1994 |
| WO | WO 94/20127 A1 * | 9/1994 |
| WO | WO 95/12313 | 5/1995 |

OTHER PUBLICATIONS

Ngo et al. The Protein Folding Problem and Tertiary Structure Prediction, Merz & LeGrand, Birkhauser Boston, pp. 491-495, 1994.*
Chicz et al. J. Exp. Med. 178: 27-47, Jul. 1993.*
Steinman et al. Cell 80/1: 7-10, Jan. 1995.*
Smilek et al. PNAS USA 88: 9633-9637, 1991.*
Chen et al. J. Immunol. 157: 3783-3790, 1996.*
Anderton et al. Immunol. 104: 367-376, 2001.*
Rammensee et al. MHC Ligands and Peptide Motifs. Springer, NY, USA Landes Bioscience 1997, pp. 204-205.*
Schwartz and Kipnis. The Neuroscientist 8/5: 405-413, 2002.*
Sercarz, E. E. Nature Biotechnology. 21/9: 1017-1019, 2003.*
Tisch and McDevitt. PNAS USA 91: 437-438, 1994.*
Karin et al. J. exp. Med. 180: 2227-2237, 1994.*
Ohashi et al. Dev. Neuroscience 17/3: 189, Jul. 8-10, 1995, Abstract.*
Kondo and Ohashi. Nippon Rinsho. Japanese Journal of Clin. Med. 52/11: 2940-5, Nov. 1994, Abstract.*
Ohashi et al. J. Neuroimmunology 54/1-2: 186, Oct. 1994, Abstract.*
Rammensee et al. MHC Ligands and Peptide Motifs. 1997, Landes Bioscience, Austin TX, USA, pp. 200 and 227.*
Resche et al. Immunogenetics. 2004, vol. 56, pp. 405-419.*
Schwartz, M. and Kipnis, J. The Neuroscientist. 2002, vol. 8, No. 5, pp. 405-413.*
De Bruijn et al. Eur. J. Immunol. 1991, vol. 27, pp. 2963-2970.*
Wucherpennig et al. PNAS USA. Dec. 1995, vol. 92, pp. 11935-11939.*
Registry Accession No. 160218-02-0 (Jan. 18, 1992).*
Registry Accession No. 155029-62-2 (May 13, 1994).*
Gregersen, P.K. et al., "The Shared Epitope Hypothesis: An approach to Understanding The Molecular Genetics of Susceptibility to Rheumatoid Arthritis", *Arthritis Rheum.*, 30:1205-1213 (1987).
Oldstone, M.B.A., "Molecular Mimicry and Autoimmune Disease", *Cell*, 50:819-820 (1987).
Scharf, S. et al., "Sequence Analysis of the HLA-Drβ and HLA-DQβ Loci from Three Pemphigus *Vulgaris Patients*", *Human Immunol*, 22:61-69 (1988).
Sinha, A. et al., "A Newly Characterized HLA-DQ Allele Associated with Pemphigus Vulgaris", *Science*, 239:1026-1029 (1988).
Ahmed, A.R. et al., "Major histocompatibility complex haplotype studies in Ashkenazi Jewish patients with pemphigus vulgaris", *Proc. Natl. Acad. Sci. (USA)*, 87:7658-7662 (1990).
Jardetzky, T.S. et al., "Peptide binding to HLA-DR1: a peptide with most residues substituted to alanine retains MHC binding", *EMBO J.*, 9(6):1797-1803 (1990).
Ota, K. et al., "T-cell recognition of an immuno-dominant myelin basic protein epitope in multiple sclerosis", *Nature*, 346:183-187 (1990).
Pette, M. et al. "Myelin autoreactivity in multiple sclerosis: Recognition of myelin basis protein in the context of HLA-DR2 products by T lymphocytes of multiple sclerosis patients and healthy donors", *Proc. Natl. Acad. Sci. (USA)*, 87: 7968-7972 (1990).

(Continued)

*Primary Examiner*—Christina Chan
*Assistant Examiner*—Marianne DiBrino
(74) *Attorney, Agent, or Firm*—Fish & Neave IP Group Ropes & Gray, LLP

(57) ABSTRACT

The present invention provides isolated peptides relating to the autoimmune diseases pemphigus vulgaris and multiple sclerosis. The peptides relating to pemphigus vulgaris are self epitopes and those relating to multiple sclerosis are foreign antigens derived from human pathogens which are implicated in the aetiology and remissions of the disease. Pharmaceutical preparations for tolerizing and/or immunizing individuals are provided as well as methods relating thereto. Methods are provided for identifying other self and non-self epitopes involved in human autoimmune disease and similar paharmaceutical preparations and methods of use for these epitopes are also provided.

2 Claims, No Drawings

OTHER PUBLICATIONS

Amagai, M. et al., "Autoantibodies against a Novel Epithelial Cadherin in Pemphigus Vulgaris, a Disease of Cell Adhesion", *Cell*, 67:869-877 (1991).

Brown, L.R. et al., "Recognition of the influenza hemaglutinin by class II MHC-restricted T lymphocytes and antibodies, I. Site definition and implications for antigen presentation and T lymphocyte recognition" *J. Immunol*, 147(8):2677-2684 (1991).

Busch, R. et al., "Effect of natural polymorphism at residue 86 of the HLA-DR β chain on peptide binding", *J. Immunol.*, 147(4):1292-1298 (1991).

Jardetzky, T.S. et al., "Identification of self peptides bound to purified HLA-B27", *Nature*, 353:326-329 (1991).

Lanchbury, J & G. Panavi, "Genetics Of RA: The HLA Shared Epitope Hypothesis And Its Implications," *Br. J. Rheumatol*, 30(Suppl 2):6-9 (1991).

O'Sullivan, D. et al., On The Interaction Of Promiscuous Antigenic Peptides With Different Dr Alleles; Identification of common structural motifs, *J. Immunol*, 147(8):2663-2669 (1991).

Wucherpfennig, K. et al., "T-cell recognition of myelin basic protein", *Immunol, Today*, 12(8):277-282 (1991).

Amagai, M. et al., "Autoantibodies Against the Amino-terminal Cadherin-like Binding Domain of Pemphigus Vulgaris Antigen are Pathogenic", *J. Clin. Invest.*, 90:919-926.

Lehmann, P. et al., Spreading of T-cell autoimmunity to cryptic determinants of an autoantigen, *Nature*, 358:155-157 (1992).

Marsh, S. et al., "HLA class II nucleotide sequences", *Human Immunol*, 35:1-17 (1992).

Chicz, R. et al., Predominant naturally processed peptides bound to HLA-DR1 are derived from MHC-related molecules and are heterogeneous in size, *Nature*, 358:764-768 (1992).

Alexander J. et al., "Functional Consequences of Engagement of the T Cell Receptor By Low Affinity Ligands", *J. Immunol.*, 150(1):1-7 (1993).

Brown, J.H. et al., "Three-dimensional structure of the human class II histocompatibility antigen HLA-DR1", *Nature*, 364:33-39 (1993).

Chicz, R.M. et al., "Specificity and Promiscuity among Naturally Processed Peptides Bound to HLA-DR Alleles", *J. Exp. Med.*, 178:27-47 (1993).

Hammer, J. et al., "Promiscuous and Allele-Specific Anchors in HLA-DR-Binding Peptides", *Cell*, 74:197-203 (1993).

Kaufman, D.L., et al., "Spontaneous loss of T-cell tolerance to glutamic acid decarboxylase in murine insulin-dependent diabetes", *Nature*, 366:69-71 (1993).

Madden, D.R. et al., "The Antigenic Identity of Peptide-MHC Complexes: A Comparison of the Conformation of Five Viral Peptides Presented by HLA-A2" , *Cell*, 75:693-708 (1993).

Sloan-Lancaster, J. et al., "Induction of T-cell anergy by altered T-cell-receptor ligand on live antigen-presenting cells", *Nature*, 363:156-159 (1993).

Tisch, R., et al., "Immune response to glutamic acid decarboxylase correlates with insulitis in non-obese diabetic mice", *Nature*, 366:72-75 (1993).

Reay, P. et al., Use of Global Amino Acid Replacements to Define the Requirements for MHC Binding and T cell Recognition of Moth Cytochrome c (93-103), *J. Immunol*, 150:3946-3957 (1994).

Rotschke, O. et al., "Origin, Structure and motifs of naturally processed MHC class II ligands", *Current Opinion Immunol*, 6:45-51 (1994).

Sloan-Lancaster, J. et al., "Partial T Cell Signaling: Altered Phospho-ζ and Lack of Zap70 Recruitment in APL-Induced T Cell Anergy", *Cell*, 79:913-922 (1994).

Stern, L. et al., "Crystal structure of the human class II MHC protein HLA-DR1 complexed with an influenza virus peptide", *Nature*, 368:215-221 (1994).

Tian, J. et al., "T Cell Cross-reactivity between Coxsackie virus and Glutamate Decarboxylase Is Associated with a Murine Diabetes Susceptibility Allele", *J. Exp. Med.*, 180:1979-1984 (1994).

Vogt, A. et al., Ligand Motifs of HLA-DRB5*0101 and DRB*1501 Molecules Delineated from Self Peptides, *J. Immunol.*, 151: 1665-1673 (1994).

Wucherpfennig, K. et al., "Structural Requirements for Binding of an Immunodominant Myelin Basic Protein Peptide to DR2 isotypes and for Its Recognition by Human T Cell Clones", *J. Exp. Med.* , 179:279-290 (1994).

Wucherpfennig, K. et al., "Clonal Expansion and Persistence of Human T cells Specific for an Immunodominant Myelin Basic Protein Peptide", *J. Immunol.*, 150:5581-5592 (1994).

Steinman, L. "Escape from "Horror Autotoxicus": Pathogenesis and Treatment of Autoimmune Disease", *Cell*, 80(1):7-10 (1995).

Bankier et al., "Sequence Analysis fo the 17, 166 Base-pair E*co*RI fragment C of B95-8 Epstein-Barr Virus" *Mol. Biol. Med*. 1: 21-45 (1983).

Chambers et al., "Antigenic and Molecular Characterization of Subtype H13 Hemagglutinin of Influenza Virus" *Virology* 172: 180-188 (1989).

Dermody et al., "The S2 Gene Nucleotide Sequences of Prototype Strains of the Three Reovirus Serotypes: Characterization of Reovirus Core Protein o2" *Journal of Virology* 65(11): 5721-5731 (1991).

McGeoch et al., "DNA sequence of the region in the genome of herpes simplex virus type 1 containing the exinuclease gene and neighbouring genes" *Nucleic Acid Research* 14(8): 1434-1448 (1986).

Oltersdorf, et al. "Molecular Cloning and Characterization of Human Papillomavirus Type 7 DNA" *Virology* 149: 247-250 (1986).

Tsurumi et al. "A Single-Base Change within the DNA Polymerase Locus and Herpes Simplex Virus Tepy 2 Can Confer Resistance to Aphidicolin" *Journal of Virology* 61(2): 388-394 (1987).

Zielinski, et al. "Characterization and Regulation of the *Pseudomonas aeruginosa algC* Gene Encoding Phophomannomutase" *The Journal of Biological Chemistry* 266(15): 9754-9762 (1991).

Hogenkamp et al., "Nucleotide Sequence of the Right 10% of Adenovirus Type 12 DNA Encoding the Entire Region E4", *Nucleic Acids Research*, vol. 18, No. 10, Apr. 1990, p. 3065.

\* cited by examiner

SEQUENCE LISTING

```
<160> NUMBER OF SEQ ID NOS:  21

<210> SEQ ID NO 1
<211> LENGTH: 15
<212> TYPE: PRT
<213> ORGANISM: Homo sapiens

<400> SEQUENCE: 1

Ala Thr Gln Lys Ile Thr Tyr Arg Ile Ser Gly Val Gly Ile Asp
 1               5                  10                  15

<210> SEQ ID NO 2
<211> LENGTH: 15
<212> TYPE: PRT
<213> ORGANISM: Homo sapiens

<400> SEQUENCE: 2

Phe Gly Ile Phe Val Val Asp Lys Asn Thr Gly Asp Ile Asn Ile
 1               5                  10                  15

<210> SEQ ID NO 3
<211> LENGTH: 15
<212> TYPE: PRT
<213> ORGANISM: Homo sapiens

<400> SEQUENCE: 3
```

-continued

```
Leu Asn Ser Lys Ile Ala Phe Lys Ile Val Ser Gln Glu Pro Ala
 1               5                  10                  15

<210> SEQ ID NO 4
<211> LENGTH: 15
<212> TYPE: PRT
<213> ORGANISM: Homo sapiens

<400> SEQUENCE: 4

Thr Pro Met Phe Leu Leu Ser Arg Asn Thr Gly Glu Val Arg Thr
 1               5                  10                  15

<210> SEQ ID NO 5
<211> LENGTH: 15
<212> TYPE: PRT
<213> ORGANISM: Homo sapiens

<400> SEQUENCE: 5

Cys Glu Cys Asn Ile Lys Val Lys Asp Val Asn Asp Asn Phe Pro
 1               5                  10                  15

<210> SEQ ID NO 6
<211> LENGTH: 15
<212> TYPE: PRT
<213> ORGANISM: Homo sapiens

<400> SEQUENCE: 6

Ser Ala Arg Thr Leu Asn Asn Arg Tyr Thr Gly Pro Tyr Thr Phe
 1               5                  10                  15

<210> SEQ ID NO 7
<211> LENGTH: 15
<212> TYPE: PRT
<213> ORGANISM: Homo sapiens

<400> SEQUENCE: 7

Gln Ser Gly Thr Met Arg Thr Arg His Ser Thr Gly Gly Thr Asn
 1               5                  10                  15

<210> SEQ ID NO 8
<211> LENGTH: 15
<212> TYPE: PRT
<213> ORGANISM: Herpes simplex

<400> SEQUENCE: 8

Phe Arg Gln Leu Val His Phe Val Arg Asp Phe Ala Gln Leu Leu
 1               5                  10                  15

<210> SEQ ID NO 9
<211> LENGTH: 15
<212> TYPE: PRT
<213> ORGANISM: Adenovirus type 12

<400> SEQUENCE: 9

Asp Phe Glu Val Val Thr Phe Leu Lys Asp Val Leu Pro Glu Phe
 1               5                  10                  15

<210> SEQ ID NO 10
<211> LENGTH: 15
<212> TYPE: PRT
<213> ORGANISM: Pseudomonas aeruginosa

<400> SEQUENCE: 10

Asp Arg Leu Leu Met Leu Phe Ala Lys Asp Val Val Ser Arg Asn
```

<210> SEQ ID NO 11
<211> LENGTH: 15
<212> TYPE: PRT
<213> ORGANISM: Human Papillomavirus type 7

<400> SEQUENCE: 11

Ile Gly Gly Arg Val His Phe Phe Lys Asp Ile Ser Pro Ile Ala
 1               5                  10                  15

<210> SEQ ID NO 12
<211> LENGTH: 15
<212> TYPE: PRT
<213> ORGANISM: Epstein-Barr virus

<400> SEQUENCE: 12

Thr Gly Gly Val Tyr His Phe Val Lys Lys His Val His Glu Ser
 1               5                  10                  15

<210> SEQ ID NO 13
<211> LENGTH: 15
<212> TYPE: PRT
<213> ORGANISM: Influenza virus type A

<400> SEQUENCE: 13

Tyr Arg Asn Leu Val Trp Phe Ile Lys Lys Asn Thr Arg Tyr Pro
 1               5                  10                  15

<210> SEQ ID NO 14
<211> LENGTH: 15
<212> TYPE: PRT
<213> ORGANISM: Reovirus type 3

<400> SEQUENCE: 14

Met Ala Arg Ala Ala Phe Leu Phe Lys Thr Val Gly Phe Gly Gly
 1               5                  10                  15

<210> SEQ ID NO 15
<211> LENGTH: 15
<212> TYPE: PRT
<213> ORGANISM: Herpes simplex virus

<400> SEQUENCE: 15

Gly Gly Arg Arg Leu Phe Phe Val Lys Ala His Val Arg Glu Ser
 1               5                  10                  15

<210> SEQ ID NO 16
<211> LENGTH: 15
<212> TYPE: PRT
<213> ORGANISM: Homo sapiens

<400> SEQUENCE: 16

Glu Asn Pro Val Val His Phe Phe Lys Asn Ile Val Thr Pro Arg
 1               5                  10                  15

<210> SEQ ID NO 17
<211> LENGTH: 5
<212> TYPE: PRT
<213> ORGANISM: Artificial Sequence
<220> FEATURE:
<221> NAME/KEY: VARIANT
<222> LOCATION: (1)
<223> OTHER INFORMATION: Xaa at position 1 is either Val, Leu, Ile, Met,
      or Phe
<221> NAME/KEY: VARIANT

```
<222> LOCATION: (3)
<223> OTHER INFORMATION: Xaa at position 3 may be any amino acid
<221> NAME/KEY: VARIANT
<222> LOCATION: (4)
<223> OTHER INFORMATION: Xaa at position 4 is either Val, Leu, Ile, Met,
      Phe, Tyr, or Trp
<223> OTHER INFORMATION: Description of Artificial Sequence: Amino acid
      sequence motif

<400> SEQUENCE: 17

Xaa His Xaa Xaa Lys
 1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Amino acid
      sequence motif
<221> NAME/KEY: VARIANT
<222> LOCATION: (1)
<223> OTHER INFORMATION: Xaa at position 1 is either Val, Leu, Ile, Ala,
      or Met
<221> NAME/KEY: VARIANT
<222> LOCATION: (2)
<223> OTHER INFORMATION: Xaa at position 2 is either Val, Leu, Ile, Ala,
      or Met
<221> NAME/KEY: VARIANT
<222> LOCATION: (3)
<223> OTHER INFORMATION: Xaa at position 3 is either His, Asn, Gln, or
      Phe
<221> NAME/KEY: VARIANT
<222> LOCATION: (5)
<223> OTHER INFORMATION: Xaa at position 5 is either Phe, Tyr, Trp, Val,
      Leu, Ile, Ala, or Met
<221> NAME/KEY: VARIANT
<222> LOCATION: (6)
<223> OTHER INFORMATION: Xaa at position 6 is either Lys or Arg

<400> SEQUENCE: 18

Xaa Xaa Xaa Phe Xaa Xaa
 1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Amino acid
      sequence motif
<221> NAME/KEY: VARIANT
<222> LOCATION: (1)
<223> OTHER INFORMATION: Xaa at position 1 is either Phe, Tyr, Trp, Val,
      Leu, Ile, Ala, or Met
<221> NAME/KEY: VARIANT
<222> LOCATION: (2)
<223> OTHER INFORMATION: Xaa at position 2 is either His, Asn, Gln, or
      Phe
<221> NAME/KEY: VARIANT
<222> LOCATION: (4)
<223> OTHER INFORMATION: Xaa at position 4 is either Phe, Tyr, Trp, Val,
      Leu, Ile, Ala, or Met
<221> NAME/KEY: VARIANT
<222> LOCATION: (5)
<223> OTHER INFORMATION: Xaa at position 5 is either Lys or Arg

<400> SEQUENCE: 19

Xaa Xaa Phe Xaa Xaa
 1               5

<210> SEQ ID NO 20
<211> LENGTH: 5
```

```
<212> TYPE: PRT
<213> ORGANISM: Artificial Sequence
<220> FEATURE:
<223> OTHER INFORMATION: Description of Artificial Sequence: Amino acid
      sequence motif
<221> NAME/KEY: VARIANT
<222> LOCATION: (1)
<223> OTHER INFORMATION: Xaa at position 1 is either Val, Leu, Ile, Ala,
      or Met
<221> NAME/KEY: VARIANT
<222> LOCATION: (2)
<223> OTHER INFORMATION: Xaa at position 2 is either His, Phe, Tyr, or
      Trp
<221> NAME/KEY: VARIANT
<222> LOCATION: (3)
<223> OTHER INFORMATION: Xaa at position 3 is either Phe, Tyr, Trp, Val,
      Leu, or Ile
<221> NAME/KEY: VARIANT
<222> LOCATION: (4)
<223> OTHER INFORMATION: Xaa at position 4 is either Phe, Tyr, Trp, Val,
      Leu, or Ile

<400> SEQUENCE: 20

Xaa Xaa Xaa Xaa Lys
 1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Amino acid
      sequence motif
<221> NAME/KEY: VARIANT
<222> LOCATION: (1)
<223> OTHER INFORMATION: Xaa at position 1 is either Val, Leu, Ile, Met,
      or Phe
<221> NAME/KEY: VARIANT
<222> LOCATION: (2)
<223> OTHER INFORMATION: Xaa at position 2 may be any amino acid
<221> NAME/KEY: VARIANT
<222> LOCATION: (3)
<223> OTHER INFORMATION: Xaa at position 3 may be any amino acid
<221> NAME/KEY: VARIANT
<222> LOCATION: (4)
<223> OTHER INFORMATION: Xaa at position 4 is either Lys or Arg
<221> NAME/KEY: VARIANT
<222> LOCATION: (5)
<223> OTHER INFORMATION: Xaa at position 5 may be any amino acid
<221> NAME/KEY: VARIANT
<222> LOCATION: (6)
<223> OTHER INFORMATION: Xaa at position 6 is either Ser, Thr, Asn, or
      Val

<400> SEQUENCE: 21

Xaa Xaa Xaa Xaa Xaa Xaa
 1               5
```

PREPARATIONS FOR INDUCING IMMUNOTOLERANCE AND USES THEREFOR

REFERENCE TO RELATED APPLICATIONS

This is a divisional of U.S. Ser. No. 08/400,796 filed on Mar. 7, 1995, now U.S. Pat. No. 5,874,531.

The present invention was supported, in part, by grant CA47554 from the National Institutes of Health. Therefore, the government may have certain rights in the invention.

FIELD OF THE INVENTION

The present invention relates to the field of immunology and, in particular, to the identification of self and non-self antigens implicated in human autoimmune responses. The invention relates to methods of identifying such self and non-self antigens and provides examples of such antigens relating to multiple sclerosis and pemphigus vulgaris. The invention also relates to the use of such antigens for in vitro assays, animal models, therapeutic agents and vaccines.

BACKGROUND OF THE INVENTION

Human autoimmune diseases have a striking genetic association with particular alleles of major histocompatability complex ("MHC") class I or class II genes. The field was established by the seminal discovery of HLA-B27 linked susceptibility to ankylosing spondylitis, a chronic inflammatory joint disease (Brewerton et al., 1973; Schlosstein et al., 1973). MHC associated susceptibility has now been documented for a variety of human autoimmune diseases, including insulin dependent diabetes mellitus (IDDM), rheumatoid arthritis (RA), pemphigus vulgaris (PV), multiple sclerosis (MS) and myasthenia gravis (MG), just to name a few (Todd et al., 1987; Ahmed et al., 1990; Ahmed et al. 1991; Lanchbury & Panayi, 1991; Spielman & Nathenson, 1982; Protti et al., 1993).

The MHC locus most commonly associated with autoimmune disease is the HLA-DRβ locus (also known as DRB1), a highly polymorphic locus with over fifty known alleles. For example, a large body of epidemiological work has documented the association of rheumatoid arthritis with the DR4 (DRB1*0401, DRB1*0404) and DR1 (DRB1*0101) alleles, with the DR4 alleles conferring a higher risk than DR1 (Lanchbury & Panayi, 1991). The risk is dramatically increased when the subject is homozygous or heterozygous for DRB1*0401 and/or DRB1*0404. The observation that arthritis is associated with three DR alleles that are structurally similar led to the development of the 'shared epitope' hypothesis as DRB1*0401, 0404 and 0101 share critical polymorphic residues in the DRβ 67-71 cluster (Gregersen et al. 1987; Lanchbury & Panayi, 1991). These residues (in particular DRβ 71) appear to be critical in defining the selectivity of peptide binding to the disease associated molecules.

Pemphigus vulgaris is an autoimmune disease of the skin in which high titer autoantibody production to an epidermal cell adhesion molecule (desmoglein 3) results in a loss of keratinocyte adhesion (acantholysis) and severe blister formation (Amagai et al., 1991). In different ethnic groups the disease is associated either with a DR4 allele (DRB1*0402) or with a rare DQ1 allele (DQB1*05032); only a small fraction of PV patients have neither susceptibility gene (Ahmed et al., 1991; Ahmed et al., 1990; Scharf et al., 1988b). The DR4 subtype associated with pemphigus differs only at three positions in the DRβ 67-71 cluster from the DR4 subtype associated with RA. The PV associated molecule has a negative charge (Glu) at the critical position (DRβ 71); the neighboring position (DRβ 70) is also negatively charged. The DR4 subtype associated with PV is the only one that carries a negative charge at DRβ 71; a positive charge (Arg) is found at DRβ 71 in the RA associated DR4 molecules.

With respect to multiple sclerosis, recent immunological studies suggest that myelin basic protein (MBP) may be one of the important target antigens in the immunopathogenesis of the disease. Several studies have demonstrated that MBP specific T cells are clonally expanded in MS patients and in an in vivo activated state (Allegretta et al., 1990; Wucherpfennig et al., 1994b; Zhang et al., 1994). Reactivity with the immunodominant MBP(84-102) peptide is found predominantly in subjects carrying HLA-DR2 (the most common subtype of which is DRB1*1501), a genetic marker for susceptibility to MS. The MBP(84-102) epitope can also be presented by other MHC class II antigens, including HLA-DQ1 (Ota et al., 1990; Martin et al., 1990; Pette et al., 1990; Wucherpfennig et al., 1994a). In vivo, the T cell response to this peptide appears to be dominated by a few expanded clones.

While associations between MHC alleles and disease states have implicated autoimmunity in the aetiology of these diseases, a large body of clinical and epidemiological evidence suggests that infections may be important in the induction of autoimmunity. For example, particular viral infections frequently precede autoimmune myocarditis and type I diabetes (IDDM) (Rose et al., 1986; Ray et al., 1980). Environmental agents also influence the risk of developing multiple sclerosis as demonstrated by migration studies. Individuals that migrate after age 15 carry the risk for developing MS associated with their geographic origin while individuals who migrate earlier in life acquire the risk of the geographical region to which they migrated (Kurtzke, 1985). These studies are consistent with the hypothesis that a group of pathogens that are relatively ubiquitous in a certain geographic region influence the risk of developing multiple sclerosis (MS). The mechanism(s) leading to clonal expansion of MBP reactive T cells remain to be identified but could involve recognition of viral peptides with sufficient structural similarity to the immunodominant MBP peptide. The initiation of autoimmunity by such a mechanism could then lead to sensitization to other CNS self antigens by determinant spreading (Lehmann et al., 1992; Kaufman et al. 1993; Tisch et al., 1993). Consonant with this hypothesis, it has been noted that inflammatory CNS disease can follow infection with a number of common viral pathogens, such as measles and rubella. On the other hand, the absence of virus in the CNS of these patients and reactivity to myelin basic protein in these patients suggest an autoimmune mechanism (Johnson et al., 1984).

Efforts to identify sequence homologies between self peptide epitopes that might be involved in autoimmunity and various bacterial and viral pathogens have therefore been made. These homology searches have focused on alignments with sequence identity. No success has been reported using such alignments in identifying epitopes from pathogens that could cross react with presumably pathogenic T cell lines from human patients with autoimmune disease (Oldstone, 1990). A sequence identity was recently found between an epitope in a Coxsackie virus protein and GAD65, suspected of being an autoantigen in diabetes. These peptides could reciprocally generate polyclonal T cell lines from mice that cross react with the other peptides (Tian, et al., 1994). No evidence, however, was provided that these peptides could stimulate clones from diabetic mice (or humans).

Recent developments in the field, in particular the identification of allele specific peptide binding motifs have transformed the field (Madden et al., 1991; Rötschke & Falk, 1991). Based on this knowledge the structural basis for MHC linked susceptibility to autoimmune diseases can be reassessed at a level of detail sufficient for solving long-standing questions in the field. Motifs for peptide binding to several MHC class I and class II molecules have been defined by sequence analysis of naturally processed peptides and by mutational analysis of known epitopes. MHC class I bound peptides were found to be short (generally 8-10 amino acids long) and to possess two dominant MHC anchor residues; MHC class II bound peptides were found to be longer and more heterogeneous in size (Madden et al., 1991; Rötschke & Falk, 1991; Jardetzky et al. 1991, Chicz et al. 1992, 1993). Due to the size heterogeneity, however, it has proven more difficult to define MHC class II binding motifs based on sequence alignments. More recently, a crystal structure for HLA-DR1 demonstrated that there is a dominant hydrophobic anchor residue close to the N-terminus of the peptide and that secondary anchor residues are found at several other peptide positions (Brown et al., 1993). Even this work, however, could not provide a detailed description of the binding pockets of HLA-DR proteins, the particular residues involved in the formation of these pockets or the structural requirements or antigens for MHC binding.

In the present disclosure, a detailed description of the HLA-DR antigen binding pockets is provided (Stern et al., 1994). With this information, together with functional information defining those amino acids of the self or non-self antigen that are needed for MHC binding and TCR contact (e.g., Wucherpfennig et al. 1994, 1995), binding motifs for the various HLA-DR allotypes may be developed, self epitopes involved in autoimmune disease may be identified and a method is provided for identifying bacterial and viral epitopes which may initiate a human autoimmune response.

SUMMARY OF THE INVENTION

The present invention provides, in one aspect, seven different isolated polypeptides derived from the human desmoglein 3 protein and implicated as self epitopes in the autoimmune disease pemphigus vulgaris (PV). These peptides consist essentially of the seven amino acid sequences disclosed herein and designated SEQ ID NO.: 1 through and SEQ ID NO.: 7. In particular, the invention provides isolated peptides which consist of these sequences, the core MHC binding residues of these sequences, or the inner core MHC binding residues of these sequences.

The present invention provides, in another aspect, eight different isolated polypeptides derived from human pathogens but implicated in the aetiology of the autoimmune disease multiple sclerosis. These peptides consist essentially of the eight amino acid sequences disclosed herein and designated SEQ ID NO.: 8 through SEQ ID NO.: 15. In particular, the invention provides isolated peptides which consist of these sequences, the core MHC binding residues of these sequences, or the inner core MHC binding residues of these sequences.

In another set of embodiments, the invention provides for pharmaceutical preparations for use in tolerizing individuals to autoantigens. The preparations include a pharmaceutically acceptable carrier and an isolated human polypeptide which includes an amino acid sequence corresponding to a sequence motif for an HLA-DR protein which is associated with a human autoimmune disease. These polypeptides are capable of binding to the HLA-DR protein to form a complex which activates autoreactive T cells in subjects having the autoimmune disease. The peptides are not derived from human collagen or human myelin basic protein.

In particular embodiments, such pharmaceutical preparations are provided in which the HLA-DR protein is HLA-DR4 protein and the autoimmune disease is pemphigus vulgaris. In addition, a particular sequence motif is provided for pemphigus vulgaris and pharmaceuticals having peptides with this motif are provided. Specific embodiments of the pharmaceuticals include each of the polypeptides described above with respect to pemphigus vulgaris. Thus, methods of tolerizing an individual to a pemphigus vulgaris autoantigen are also provided.

In another set of embodiments, the invention provides for pharmaceutical preparations for use in tolerizing individuals to antigens of human pathogens which are implicated in human autoimmune disease. The preparations include a pharmaceutically acceptable carrier and an isolated human pathogen polypeptide which includes an amino acid sequence corresponding to a sequence motif for an HLA-DR protein which is associated with a human autoimmune disease. These polypeptides are capable of binding to the HLA-DR protein to form a complex which activates autoreactive T cells in subjects having the autoimmune disease.

In particular embodiments, such pharmaceutical preparations are provided in which the HLA-DR protein is HLA-DR2 protein and the autoimmune disease is multiple sclerosis. In addition, three particular sequence motifs are provided for multiple sclerosis and pharmaceuticals having peptides with at least one of these motifs are provided. Specific embodiments of the pharmaceuticals include each of the polypeptides described above with respect to multiple sclerosis. Thus, methods of tolerizing an individual to a multiple sclerosis foreign antigen are also provided.

In another aspect of the invention, pharmaceuticals are provided for vaccination against a human pathogen implicated in the aetiology of autoimmune disease. These pharmaceutical preparations include a pharmaceutically acceptable carrier and an immunogenic preparation effective to immunize against a human pathogen. The human pathogen is one which in its native form includes a polypeptide having an amino acid sequence corresponding to a sequence motif for an HLA-DR protein which is associated with the autoimmune disease. These polypeptides are capable of binding to the HLA-DR protein to form a complex which activates T cells which become autoreactive and intiate the autoimmune disease. The preparations of the present invention specifically do not include such polypeptides but, rather, include other antigens from the pathogen.

In particular embodiments, such pharmaceutical preparations are provided in which the HLA-DR protein is HLA-DR4 protein and the autoimmune disease is pemphigus vulgaris. In addition, a particular sequence motif is provided for pemphigus vulgaris and pharmaceuticals which lack peptides having this motif are provided. Specific embodiments of the pharmaceuticals include preparations lacking each of the polypeptides described above with respect to pemphigus vulgaris. Thus, methods of immunizing an individual against pathogens which may cause pemphigus vulgaris are also provided.

Similarly, pharmaceutical preparations are provided in which the HLA-DR protein is HLA-DR2 protein and the autoimmune disease is multiple sclerosis. Three particular sequence motifs are provided for multiple sclerosis and pharmaceuticals which lack peptides having any of these motifs are provided. Specific embodiments of the pharmaceuticals include preparations lacking each of the polypeptides described above with respect to multiple sclerosis. Thus, methods of immunizing an individual against pathogens which may cause multiple sclerosis are also provided.

The pharmaceutical preparations for immunizing against pathogens that may cause multiple sclerosis may particularly include inactivated forms of the pathogen in which the polypeptide corresponding to the motif are removed or recombinantly altered. Thus, the invention provides such vaccines in which the pathogen and polypeptide are, respectively, Herpes simplex virus and UL15 protein, Herpes simplex virus and SEQ ID NO.: 8, Adenovirus and Adenovirus ORF protein, Adenovirus and SEQ ID NO.: 09, *Pseudomonas aeruginosa* and phosphomannomutase protein, *Pseudomonas aeruginosa* and SEQ ID NO.: 10, Papillomavirus and L2 protein, Papillomavirus and SEQ ID NO.: 11, Epstein-Barr virus and DNA polymerase protein, Epstein-Barr virus and SEQ ID NO.: 12, Influenza virus and hemagglutinin protein, Influenza virus and SEQ ID NO.: 13, Reovirus and sigma 2 protein, Reovirus sand SEQ ID NO.: 14, Herpes simplex virus and DNA polymerase, and Herpes simplex and SEQ ID NO.: 15.

The present invention also provides general methods for evaluating a peptide for an ability to induce an autoimmune response. These methods involve choosing an MHC HLA-DR molecule associated with the autoimmune response, selecting at least two major MHC binding pockets of the HLA-DR molecule, identifying sets of amino acid residues which bind within each of the selected pockets, developing a sequence motif for the HLA-DR molecule in which the sets of amino acids define the allowed amino acids at the corresponding positions of the motif, and then comparing the amino acid sequence of the peptide to the sequence motif. Peptides which match the motif have a much greater likelihood of inducing the autoimmune disease. In addition, if there is a known epitope implicated in the disease, the method may further include selected at least one TCR contact residue of the epitope, identifying a set of amino acid residues which may serve as the TCR contact, and including this set in the motif at the appropriate position. In preferred embodiments, the motifs include restrictions on the residues at positions corresponding to at least the P1 MHC binding pocket and at least one of the P4 and P6 pockets.

In another embodiment of the invention, methods are provided specifically for identifying foreign antigens implicated in human autoimmune response. These methods include the same steps as the previously described methods, but further include a comparison of the resulting sequence motif to sets of human pathogens. In preferred embodiments, peptide sequences from one or more species in the normal human intestinal flora are excluded from consideration. In another preferred embodiment, sequences from one or more species of pathogen which is negatively correlated with the incidence of the disease are excluded. In a most preferred embodiment, the human pathogen peptides are searched and evaluated on a computer database using the motif as a search criterion.

DETAILED DESCRIPTION OF THE INVENTION

The present invention relates to a method of identifying and evaluating peptides for their ability to induce an autoimmune response or to cause autoimmune disease. In particular, the invention relates to methods of (1) evaluating self peptides for their potential involvement in autoimmune disease when the self epitope or autoantigen is unknown and (2) evaluating foreign peptides for their possible involvement in the aetiology of autoimmune disease. The invention also relates to specific peptides identified by the methods of the invention and representing self and foreign antigens implicated in, respectively, pemphigus vulgaris and multiple sclerosis.

The methods rely upon the development of amino acid sequence motifs to which potential self or foreign epitopes may be compared. Each motif describes a finite set of amino acid sequences in which the residues at each (relative) position may be (a) restricted to a single residue, (b) allowed to vary amongst a restricted set of residues, or (c) allowed to vary amongst all possible residues. For consistency in this disclosure, but without limiting the invention in any way, these sequence motifs will be symbolized as strings of characters in which (a) a position which is restricted to a single residue will be represented by the one-letter abbreviation for that residue, (b) a position which is allowed to vary amongst a set of residues will be represented by a column of the one-letter abbreviations for those residues, and (c) a position which is allowed to vary amongst all amino acid residues will be represented by an "X." As an example only, a motif might specify that the residue at a first position may be any one of the residues valine, leucine, isoleucine, methionine, or phenylalanine; that the residue at the second position must be histidine; that the residue at the third position may be any amino acid residue; that the residue at the fourth position may be any one of the residues valine, leucine, isoleucine, methionine, phenylalanine, tyrosine or tryptophan; and that the residue at the fifth position must be lysine. Such a motif would be represented by the following character string:

| V | H | X | V | K | (SEQ ID NO:17) |
|---|---|---|---|---|---|
| L |   |   | L |   |   |
| I |   |   | I |   |   |
| M |   |   | M |   |   |
| F |   |   | F |   |   |
|   |   |   | Y |   |   |
|   |   |   | W |   |   |

In one aspect of the present invention, sequence motifs are developed by analysis of the binding domains or binding pockets of major histocompatibility complex HLA-DR proteins and/or the T cell receptor ("TCR") contact points of epitopes bound to MHC molecules. By providing a detailed structural analysis of the HLA-DR residues involved in forming the MHC binding pockets, one is enabled to make predictions of sequence motifs for binding to any of the HLA-DR proteins.

In another aspect of the present invention, sequence motifs developed by the methods disclosed herein may be used to identify self peptide epitopes involved in an autoimmune response when the autoantigen is known or suspected.

In another aspect of the present invention, methods of identifying foreign peptide epitopes implicated in autoimmune disease are provided. These methods involve the use of MHC and/or TCR binding motifs to identify peptides derived from certain classes of organisms or pathogens which may initiate human autoimmune response. In this aspect, the motifs may be developed according to the methods of the present invention or by other means known in the art.

Using these sequence motifs as search, evaluation, or design criteria, one is enabled to identify classes of peptides which have a reasonable likelihood of binding to a particular MHC molecule and of interacting with a T cell receptor to induce T cell and/or autoimmune response. Use of these motifs, as opposed to pure sequence homology (which excludes many peptides which are antigenically similar but quite distinct in sequence) or sequence homology with unlimited "conservative" substitutions (which admits many peptides which differ at critical highly conserved sites), represents a significant advance in the ability of one of ordinary skill in the art to evaluate particular peptides for potential involvement in autoimmune disease and to search computer databases of peptide sequences to identify self and foreign peptides which may be involved in autoimmune response. In addition, the use of MHC and/or TCR binding motifs to search limited databases for foreign peptides which may be implicated in the aetiology of autoimmune disease is a novel application of the concept of binding motifs.

Detailed examples of the practice of the present invention are presented below. The methods of the invention have now been used to identify the previously unknown self peptide epitopes involved in the autoimmune disease pemphigus vulgaris. In addition, the methods have been used to identify a class of foreign peptides which may be involved in the initiation of autoimmune response in multiple sclerosis (for which the self epitope had previously been identified).

Thus, in another embodiment, the invention provides these peptides, in isolated form, which may be used in various diagnostic and therapeutic methods and products alluded to below.

I. The MHC Class II HLA-DR Molecular Mimicry Motif

The HLA-DR binding site is characterized by five major pockets which may bind the amino acid side chains of antigens (Stern et al., 1994, the entire disclosure of which is incorporated herein by reference). See FIG. 1. The amino acid residue of the antigen which binds in the first major pocket is designated P1. The remaining residues may then be numbered by their positions relative to P1 (with positive numbers increasing toward the carboxy terminus and negative numbers increasing toward the amino terminus):

P-i . . . P-1 P1 P2 P3 P4 . . . Pj

Thus, the first major pocket of an HLA-DR molecule, by definition, binds the side chain of residue P1 on an antigen. The remaining major pockets bind residues P4, P6, P7 and P9. These residues are defined as the major MHC contact residues.

The amino acid side chains of residues P-1, P2, P3, P5, P8, and P11 are oriented away from the HLA-DR binding site and, therefore, are available as contact residues for a T cell receptor (TCR). All of these residues are defined as TCR contact residues.

A. The MHC Contact Residues

The first major pocket of the HLA-DR molecule is strongly hydrophobic. It is formed by a stretch of residues at about positions 85, 86, 89 and 90 of the β chain, a stretch of residues at about positions 31, 32 and 34 of the α chain, and side chains from residues at about positions 7 and 43 of the α chain. For example, in HLA-DR1 (DRA, DRB1*0101), the first pocket is formed by residues β85 (Val), β86 (Gly), β89 (Phe), β90 (Thr), α31 (Ile), α32 (Phe), α34 (Phe), α7 (Ile), and α43 (Trp). The corresponding residues for other HLA-DR alleles are known in the art (see, e.g., Marsh and Bodmer, 1992, incorporated by reference herein) and are available through genetic databases.

Although most of the residues that shape the P1 pocket are from the highly conserved DRα chain, the size and nature of this pocket varies due to polymorphisms in the β chain residues involved in the pocket. For the DRB1*0101 protein, the pocket is large and hydrophobic and can accommodate any of the aliphatic or aromatic residues. Polymorphism at the β residues, however, may alter the binding capacity of the P1 pocket. For example, the β86 residue is known to be polymorphic. Most commonly, this site is occupied by either Gly or Val. Generally, when Gly is present at β86 (as in DRB1*0101), any of the aliphatic or aromatic residues may bind within the pocket. When Val is present, however, the pocket is smaller and Tyr and Trp cannot be accommodated. Thus, when β86 is Gly, position P1 of the molecular mimicry motif may consist of residues chosen from V, L, I, A, M, F, Y, W and when β86 is Val, position P1 of the motif may consist of residues chosen from V, L, I, A, M, F. Similar considerations apply to the other β residues of the P1 pocket.

The P4 pocket of HLA-DR molecules is also a relatively large, shallow, hydrophobic pocket oriented across the antigen binding site. This pocket can bind a variety of large aliphatic side chains which can maintain hydrophobic interactions along the side and floor of the pocket. The pocket is formed by a stretch of residues at about positions 70, 71, 74 and 78 of the β chain, and side chains from residues at about position 13 of the β chain and about position 9 of the α chain. For example, in HLA-DR1 (DRA, DRB1*0101), the P4 pocket is formed by residues β70 (Gin), β71 (Arg), β74 (Ala), β78 (Tyr), β13 (Phe), and α9 (Gln). The corresponding residues for other HLA-DR alleles are known in the art (see, e.g., Marsh and Bodmer, 1992) and are available through genetic databases.

Like the P1 pocket, the P4 pocket is largely hydrophobic but its binding capacity is affected by polymorphisms at the β residues involved in the pocket. For example, different DR alleles have differently charged residues at position β71: In DRB1*0404, B71 is occupied by a positively charged Arg residue whereas in DRB1*0402 β71 is a negatively charged Glu residue. Thus, although this pocket can generally bind a variety of aliphatic or aromatic side chains (e.g., V, L, I, A, M, F, Y, W), positively charged P4 antigen residues are disfavored when β71 is positively charged and, similarly, negatively charged P4 residues are disfavored when β71 is also negative. Similar considerations apply to the other β residues of the P4 pocket. Note that some residues may be involved in forming each of two adjacent pockets (e.g., β13 in the P4 and P6 pockets) and therefore the occupancy of one of these pockets by a particular amino acid may influence the occupancy of the other.

The P6 pocket of HLA-DR molecules is a relatively shallow pocket with a preference for smaller (e.g., A, G) P6 antigen residues. The pocket is formed by the highly conserved α11, α62, α65 and α66 residues and the highly polymorphic β11 and β13 residues of the HLA-DR protein. For example, in HLA-DR1 (DRA, DRB1*0101), the P6 pocket is formed by residues α11 (Glu), α62 (Asn), α65 (Val), α66 (Asp), β11 (Leu) and β13 (Phe). The corresponding residues for other HLA-DR alleles are known in the art (see, e.g., Marsh and Bodmer, 1992) and are available through genetic databases.

Although there are only two β chain residues in the P6 pocket, they vary widely amongst the DR alleles. With a large Phe residue at B13 (as in DRB1*0101), the P6 residue is preferably one of the small residues (e.g., A, G). In other DR alleles, however, β13 is occupied by smaller or more polar residues such as the β13 (His) of DRB1*0401. For such alleles, the P6 motif may include somewhat larger and polar residues (e.g., S, T, V) but should still avoid the largest and aromatic residues. Finally, in some alleles, β11 and β13 are both serine residues (e.g., DRB1*1101) and for these cases more hydrophilic or hydrogen bonding residues may be included in the motif.

The P7 pocket of HLA-DR molecules is also a relatively shallow pocket. The pocket is formed by five residues of the β chain: β28, β47, β61, β67 and β71. For example, in HLA-DR1 (DRA, DRB*0101), the P7 pocket is formed by residues β28 (Glu), β47 (Tyr), β61 (Trp), β67 (Leu) and β71 (Arg). The corresponding residues for other HLA-DR alleles are known in the art (see, e.g., Marsh and Bodmer, 1992) and are available through genetic databases. This pocket does not appear to contribute greatly to the specificity of HLA-DR1 but may be important in other alleles.

The P9 pocket of HLA-DR molecules is generally a small hydrophobic pocket and, therefore, small hydrophobic residues are preferred at the P9 position of the antigen. This pocket is formed by the conserved α chain residues α69, α72, α73 and α76 and by the polymorphic β chain residues β9 and β57. For example, in HLA-DR1 (DRA, DRB1*0101) the P9 pocket is formed by α69 (Asn), α72 (Ile), α73 (Met), α76 (Arg), β9 (Trp) and β57 (Asp). The corresponding residues for other HLA-DR alleles are known in the art (see, e.g., Marsh and Bodmer, 1992) and are available through genetic databases.

The P6, P7 and P9 pockets appear to be less important than the P1 and P4 pockets in binding to DR molecules but they may be more important in binding to other isotypes (e.g., the P9 pocket of DQ may be important).

B. The TCR Contact Residues

When there is no known or suspected antigen involved in an autoimmune response, the positions of the sequence motif corresponding to the TCR contact residues may be left unrestricted. That is, absent a known or suspected antigen, the TCR contact positions of the motif are preferably allowed to vary amongst all of the amino acids.

When, on the other hand, there is a known or suspected antigen involved in an autoimmune response, at least some of the motif positions corresponding to the TCR contact residues may be restricted according to the sequence of the antigen. Thus, for example, the P2 and/or P3 and/or P5 positions of the motif may be restricted to only those residues found at the corresponding positions of the antigen. Alternatively, at least some of the TCR contact residues of the motif may be restricted not just to the corresponding residues of the antigen but may be allowed to vary amongst similarly charged and/or structurally similar residues (e.g., K and R). It should be noted, however, that greater conservatism with respect to the TCR contact residues of the motif is justified by the presumably greater specificity of TCR binding relative to the known promiscuity of MHC binding.

C. Developing an HLA-DR Sequence Motif

Given the present disclosure of the HLA-DR residues involved in the formation of the P1, P4, P6, P7 and P9 MHC binding pockets, and given the nucleotide or corresponding amino acid sequence of any particular HLA-DR allele, one is now enabled to develop a sequence motif useful in evaluating or predicting the ability of peptides to bind to that MHC protein. When a particular antigen is known to (or is suspected of) binding to the MHC protein, the TCR contact residues of that antigen may also be considered in the motif.

The method first requires the selection of two or more of the MHC binding pockets for which the choice of peptide residues will be restricted at the corresponding positions of the motif. One may select all five of the major binding pockets and develop a motif in which the corresponding five positions of the motif are restricted or one may select fewer and develop a less restricted motif. As will be obvious to one of ordinary skill in the art, a more restricted motif will identify a lesser number of peptides in a database search and a less restricted motif will identify a greater number of peptides. In all instances, at least two of the major binding pockets should be selected. When fewer than all five MHC binding pockets are selected, it is preferred that at least one is P1 and that a second is chosen from P4, P6 and P9.

Either before or after the pockets to be restricted by the motif are selected, the set of amino acid side chains likely to bind within each of those pockets and, therefore, the set of amino acid residues that will define the corresponding positions of the motif, must be determined. This may be accomplished by one of ordinary skill in the art by considering the amino acid residues which form the pocket. These residues, identified in Section A above, will determine the size and nature (i.e., hydrophobic, hydrophilic, positively charged, negatively charged, uncharged) of the pocket and consequently, the side chains which may bind within the pocket. Reference may be had to FIG. 1 of Stern et al., 1994 during these considerations but will become increasingly unnecessary as one develops familiarity with the variations of the pockets.

As a general matter, in light of the identification of the residues forming the MHC binding pockets of the HLA-DR proteins disclosed herein, one of ordinary skill in the art can easily develop a sequence binding motif for any HLA-DR protein for which these residues are known for two or more binding pockets. The major considerations are size, hydrophobicity and charge. In light of the present disclosure, each of these considerations may be addressed according to well-known principles. A baseline is disclosed herein for each pocket for the DRB1*0101 allele. Relative to this HLA-DR protein, one of ordinary skill is enabled to develop motifs for other HLA-DR alleles. Thus, substitutions which lead to larger/smaller pockets suggest that the corresponding motif positions should be restricted so as to permit smaller/larger residues. Similarly, more/less hydrophobic pockets suggest that the corresponding motif positions should be restricted to more/less hydrophobic residues. Finally, positively/negatively charged pockets suggest that positively/negatively charged residues should be excluded and negatively/positively charged residues may be included at the corresponding motif positions. As noted above, the present disclosure enables one of ordinary skill to develop motifs based upon well-established principles.

For example, and not by means of limitation, consider the P1 pocket of the HLA-DR protein. The residues forming this pocket in the DRB1*0101 were described above. For DRB1*0101, the P1 pocket is large and hydrophobic and can accommodate any of the aliphatic or aromatic residues (e.g., V, L, I, A, M, F, Y, W). For the DRB1*1602 protein the same is true. On the other hand, in the DRB1*1501 protein, the β86 position is occupied by Val instead of the Gly found in DRB1*0101 and DRB1*1602. This substitution decreases the size of the P1 pocket in this MHC protein and, as a result, the pocket cannot easily accommodate Tyr or Trp side chains. Thus, for DRB1*1501, the sequence motif at position P1 may be restricted to residues chosen from V, L, I, A, M and F.

Similarly, in light of the present disclosure, one of ordinary skill in the art may consider each of the MHC binding pockets, or only selected pockets, and develop a sequence motif for any HLA-DR protein for which the residues involved in pocket formation are known. These residues will determine both the size and nature of the pocket and, thereby, the size and nature of the residues which may bind within it. When the pocket is relatively small, the largest amino acid residues (e.g., Y, W) may be excluded from the corresponding position of the motif and, when the pocket is charged, amino acid residues of the same charge may be excluded.

If a self or foreign epitope involved in immune response is known or suspected, and particularly if its TCR contact residues can be defined through the use of responsive T cell clones, the TCR contact residues of the epitope may also be considered in developing a sequence motif. As with the MHC contact residues, all or merely some of the TCR contact residues may be restricted in the motif. And, as with the MHC positions, the restriction of more positions (or the greater restriction of any one position) will result in the identification of fewer peptides in a database search. Unlike the MHC contact residues, for which at least two positions should be restricted in the motif, it is acceptable to omit any restrictions of TCR contact residues in the motif.

If any TCR contact residue positions are restricted in the sequence motif, it is preferred that a position selected from positions P2, P3 and P5 be chosen. Because, in contrast to the relative promiscuity of MHC binding pockets, TCR contact residues appear to have greater specificity, it is preferred that any TCR contact residue positions which are restricted in the motif be rather narrowly restricted. That is, it is preferred that such positions be restricted to just the residue found at the corresponding position of the known antigen or just to residues which are highly similar in structure and charge.

For example, and as further detailed below, the MBP (85-99) peptide is known to be the autoantigen implicated in multiple sclerosis. The P3 residue of this peptide is Phe (residue 91 of MBP) and the P5 residue is Lys (residue 93 of MBP). Thus, if P3 is restricted in the motif, it is preferred that it be restricted to F or, possibly, to F and Y. Similarly, if P5 is restricted, it is preferred that it be restricted to only K or to K and the similarly charged R. Alternatively, P3 and P5 may be left unrestricted.

Obviously, MHC and TCR positions not selected for restriction may be represented by, in the notation of this disclosure, an X. Similarly, as shown in the examples below, several motifs may be developed with varying numbers of positions restricted to varying extents.

II. Identifying Self Epitopes Using Sequence Motifs

An ever increasing number of autoimmune diseases are now being associated with particular alleles of the MHC Class II HLA-DR locus. For most of these autoimmune diseases, the self epitope remains unknown. For some, however, a self protein involved in autoimmune response is known or suspected.

In one aspect of the present invention, a method is provided for identifying the self epitopes involved in autoimmune diseases associated with HLA-DR alleles. That is, by comparing human peptide sequences to the sequence motifs of the present invention, one is enabled to identify those peptides which have the highest likelihood of being the self epitopes involved in the disease.

The method may be applied to any of the autoimmune diseases for which an association with a particular HLA-DR allele is known and for which the amino acid residues forming the MHC binding pockets (or at least two of the major pockets) for that allele are known. In accordance with the method discussed herein, one may then develop one or more sequence motifs for the HLA-DR protein associated with the disease. Naturally, if the disease is associated with two or more alleles, motifs may be developed for the two or more HLA-DR proteins and, in particular, a consensus motif may be developed using the residues shared by each position of these motifs.

The sequence motif or motifs thus developed are then compared to appropriate sets of human peptide sequences. The human peptide sequences may include all known human sequences or may be limited in ways which will be obvious to one of ordinary skill in the art. For example, if the disease is restricted to particular tissues, the search may be limited to peptides found in those tissues. Conversely, peptides which are also found in unaffected tissues may be eliminated from the search pool. In the most extreme case, when the autoantigen is known or suspected but the particular epitope is unknown, the search may be limited to sequences within the autoantigen (see Example 1).

This method may be used to identify a set of peptides which match the motif and which are most likely to be self epitopes. By varying the number of positions restricted by the motifs, and/or the extent of restriction at each position, and/or the size of the search pool, the number of peptides in the set will, in all likelihood, also be varied. As noted above, at least two of the MHC contact positions (e.g., P1 and P4) should be restricted. Depending upon the number of peptides in the resultant set, a more or less restrictive motif may then be employed to reduce or expand the set. The desired size of the resultant set depends, of course, upon the subsequent intentions of the practitioner of this method.

Once a set of peptides has been identified, these peptides may optionally be screened for activity. The choice of such screens is at the discretion of the practitioner and beyond the scope of the present invention. Preferred screens, however, include in vitro tests for the ability to induce the proliferation of autoreactive T cells or to induce the secretion of lymphokines (cytokines) from these T cells or to induce other effector functions such as cytotoxicity. In some circumstances, human in vivo tests may be appropriate and in other circumstances animal models of the human disease may be available.

III. Identifying Foreign Epitopes Implicated in Human Autoimmune Disease

As noted in the Background section, epidemiological evidence has suggested that various bacterial and viral pathogens may be implicated in human autoimmune diseases and the concept of molecular mimicry pervades the literature (reviewed by Oldstone, 1990). Prior attempts to identify particular foreign epitopes involved in human autoimmune disease, however, have depended upon direct sequence similarity to known human epitopes. The results have been disappointing and, to date, no pathogens or peptides derived from pathogens have been shown to be a primary cause of human autoimmune disease.

Thus, in another aspect of the present invention, a method of identifying foreign epitopes implicated in human autoimmune disease is provided. That is, for the first time a method of identifying such foreign epitopes is provided which employs sequence motifs to identify foreign peptides which have the highest likelihood of being involved in the aetiology of human autoimmune disease.

The method may be applied to any of the autoimmune diseases for which an association with a particular MHC protein is known and for which either (1) a sequence motif has been developed by prior art methods or (2) a sequence motif may be developed by the methods of the present invention. When the self epitope is known or suspected, TCR contact residues may be included in the motif. As before, one or more motifs may be employed and differently derived motifs may be combined to develop consensus motifs.

The sequence motif or motifs thus developed may then be compared to appropriate sets of peptide sequences derived from human pathogens. This is most conveniently accomplished using genetic databases widely available to those of skill in the art. In a most preferred embodiment, the search pool is limited in one or more of the following ways: (1) only sequences from human bacterial or viral pathogens are included; (2) sequences from the normal human intestinal flora (e.g., E. coli or other Enterobacteriaceae) are excluded; and (3) sequences from pathogens are included/excluded depending upon whether the geographical or epidemiological incidence of the pathogens are positively/negatively correlated with the incidence of the autoimmune disease in question (see Example 2).

This method may be used to identify a set of foreign peptides which match the motif and which are most likely to be involved in the human disease. As before, the number of peptides in the set can be varied by using more or less restrictive motifs and/or by varying the search pool. And, as before, the resultant set of peptides may subsequently be subjected to any of a variety of known screens for activity.

IV. Self and Foreign Epitopes Identified by the Methods of the Present Invention As detailed in the examples below, the methods of the present invention have been employed (1) to identify seven self epitopes of the desmoglein 3 protein implicated in pemphigus vulgaris and (2) to identify eight foreign epitopes from human pathogens implicated in multiple sclerosis.

Each of these peptides is fifteen residues in length, partly as a result of the computer database search program used (Genetics Computer Group program "Findpatterns") but also corresponding to the size of the cleft in MHC class II molecules. The fifth position of each corresponds to the P1 residue of the antigen. Thus, the P-2 to P11 residues which span the MHC Class II binding cleft correspond to the third through fifteenth residues of these sequences. The P-1 to P9 residues which are important to MHC and TCR binding correspond to the fourth through thirteenth positions. The most important residues for MHC and TCR binding, P-1 to P6 correspond to the fourth through tenth positions of these sequences.

SEQ ID NO.: 1 through SEQ ID NO.: 7, also shown in Table 1 as PVA.1 through PVA.7, correspond to residues 78-93, 97-111, 190-204, 206-220, 251-265, 512-526 and 762-786 of the human desmoglein 3 protein. These peptides are implicated as self epitopes in pemphigus vulgaris. Already, as described in Example 1, two of these peptides have been shown to cause proliferation of T cells isolated from two patients with pemphigus.

SEQ ID NO.: 8 through SEQ ID NO.: 15, also shown in Table 2 are internal fragments of the herpes simplex virus UL15 protein, adenovirus Type 12 ORF, *Pseudomonas aeruginosa* phosphomannomutase, human Papillomavious Type 7 L2 protein, Epstein-Barr virus DNA polymerase, Influenza Type A hemagglutinin protein, Reovirus Type 3 sigma 2 protein, and herpes simplex DNA polymerase, respectively. These peptides are implicated as foreign epitopes involved in the aetiology or in remissions of multiple sclerosis. As detailed in Example 2 below, each has been shown to be capable of inducing the proliferation of autoreactive T cell clones isolated from human multiple sclerosis patients. The sequence of the MBP (85-99) peptide is disclosed as SEQ ID NO.: 16.

Each of these proteins has a variety of utilities and, therefore, in another aspect, the present invention provides each of these peptides in isolated form. In addition to the sequences of fifteen residues shown in the Sequence Listing and Tables, the present invention also embraces the fragments of these peptides corresponding to the MHC binding domain. In particular, the invention provides peptides corresponding to the P-2 to P11, P-1 to P9 and P-1 to P6 positions of each of SEQ ID NO.: 1 through SEQ ID NO.: 15. As will be obvious to one of ordinary skill in the art, however, any fragment of any of these peptides which includes at least the P1 and P4 or at least the P1 and P6 or at least the P4, P6 and P7 residues may have utility and is intended to fall within the spirit and scope of the claims. In particular, longer peptides including these peptides or peptides including at least the MHC binding and TCR contact residues described above are contemplated as equivalents.

The manner of production of these peptides is inconsequential but they may be isolated and purified from their natural sources or they may be synthesized. Because of their relatively short length, it is presently contemplated that they should be produced by synthesis. Methods of isolation, purification and synthesis of such peptides are well known in the art and need not be recited herein.

The present invention also provides products and methods using other peptides which may be identified by the methods of the present invention. These peptides, as well as those disclosed above, may be used in each of the following embodiments.

The peptides of the present invention may be used for in vitro assays to aid in the diagnosis and classification of pemphigus vulgaris and multiple sclerosis. For example, autoreactive T cells from patients with PV and MS may be tested, as in the examples below or by other known assays, for reactivity with these peptides. The ability or inability of these peptides to cause proliferation of the T cells will, in the case of pemphigus, allow for a refinement of the diagnosis by particular desmoglein 3 epitopes and, in the case of multiple sclerosis, allow further classification of the disease by cross-reactive (self and foreign epitope) types. Immune response to these peptides prior to onset of disease may also be used as an indication of susceptibility or predisposition although care should be taken so as not to induce autoantigenic response.

The peptides of the present invention may also be used in the development of animal models by immunizing animals (e.g., mice, rabbits, non-human primates) with these peptides. Animals which not only develop a response to the peptide but which also develop an autoimmune disease corresponding to the human pathology will have obvious utility as models for the human disease. Animals which develop a response to the peptide without developing any corresponding autoimmune disease, will have utility as subjects for experiments involving the selective depletion of T cells or other forms of desensitization or tolerization.

Importantly, these peptides and amino acid analogs of these peptides will have utility as therapeutic and diagnostic agents. The pathogens, viruses or bacteria from which they are derived will have utility as vaccinating agents. Some examples of the utility of these materials include the following.

The peptide may be administered in high doses to produce high dose tolerance. This process of tolerization is described in, for example, PCT patent application US93/08456 (International publication number WO 94/06828). Thus, in one set of embodiments, the invention provides for pharmaceutical preparations for use in tolerizing individuals to autoantigens. The preparations may include a pharmaceutically acceptable carrier and an isolated human polypeptide which includes an amino acid sequence corresponding to a sequence motif for an HLA-DR protein which is associated with a human autoimmune disease. These polypeptides are capable of binding to the HLA-DR protein to form a complex which activates autoreactive T cells in subjects having the autoimmune disease. By using the peptides disclosed herein or identified by the methods of the invention, such pharmaceuticals can be used to combat autoimmune response. The use of such tolerization to human autoimmune diseases is known in the art and need not be elaborated upon here. Tolerizing doses of collagen for rheumatoid arthritis and myelin basic protein for multiple sclerosis have been used. The present invention therefore specifically does not embrace these proteins. Other peptides, however, may now be identified by the present methods and be similarly used to treat autoimmune disease.

In particular embodiments, such pharmaceutical preparations are provided in which the HLA-DR protein is HLA-DR4 protein and the autoimmune disease is pemphigus vulgaris. In addition, using PV motif #1, pharmaceuticals having peptides with this motif are provided. In most preferred embodiments, the pharmaceuticals include at least one of the polypeptides of SEQ ID NO. 1 through SEQ ID NO.:7. Thus, methods of tolerizing an individual to a pemphigus vulgaris autoantigen are also provided.

In a similar set of embodiments, the invention provides for pharmaceutical preparations for use in tolerizing individuals to antigens of human pathogens which are implicated in human autoimmune disease. The preparations include a pharmaceutically acceptable carrier and an isolated human pathogen polypeptide which includes an amino acid sequence corresponding to a sequence motif for an HLA-DR protein which is associated with a human autoimmune disease. These polypeptides are capable of binding to the HLA-DR protein to form a complex which activates autoreactive T cells in subjects having the autoimmune disease. Thus, by tolerizing an individual to these antigens, T cells which are cross-reactive with the self antigen will be renedered unresponsive or anergized and protection from the disease will be afforded.

In particular embodiments, such pharmaceutical preparations are provided in which the HLA-DR protein is HLA-DR2 protein and the autoimmune disease is multiple sclerosis. In addition, using the three MS motifs disclosed herein, pharmaceuticals having peptides with at least one of these motifs are provided. Specific embodiments of the pharmaceuticals include at least one of the polypeptides disclosed as SEQ ID NO.:8 through SEQ ID NO.: 15. Thus, methods of tolerizing an individual to a multiple sclerosis foreign antigen are also provided.

In set of embodiments, pharmaceuticals are provided for vaccination against a human pathogen implicated in the aetiology of autoimmune disease. These pharmaceutical preparations include a pharmaceutically acceptable carrier and an immunogenic preparation effective to immunize against a human pathogen. The human pathogen is one which in its native form includes a polypeptide having an amino acid sequence corresponding to a sequence motif for an HLA-DR protein which is associated with the autoimmune disease. These polypeptides are capable of binding to the HLA-DR protein to form a complex which activates T cells which become autoreactive and intiate the autoimmune disease. The preparations of the present invention specifically do not include such polypeptides but, rather, include other antigens from the pathogen. That is, a vaccine is produced which specifically does not include polypeptides which correspond to the sequence motifs for the HLA-DR protein and, if known, the TCR contacts of the self epitope. Because pathogens present a wide array of antigenic determinants, one may eliminate those which correspond to the relevant sequence motif and produce a vaccine which is effective against the pathogen but which will not include peptides implicated in the autoimmune response.

Such vaccines, lacking peptides corresponding to the sequence motifs of the present invention, may be made in any convenient manner by one of ordinary skill in the art. For example, when producing an influenza vaccine, one may compare the peptide sequences of the influenza virus to sequence motifs developed according the present invention. The vaccine may then be made excluding the proteins which have the motif sequences (e.g. by using a fragment of the virus) or recombinant techniques may be used to produce a virus in which the sequences corresponding to the motif are altered such that they do not match the motif. In preferred embodiments, the altered residues are the TCR contact residues and, in particular, a substitution which alters the charge of a TCR contact residue is preferred. Similar vaccines can be developed for bacterial pathogens using, for example, only portions of the bacterium (e.g. bacterial surface proteins or membrane associated proteins) which lack a motif associated with human autoimmune disease or, again, genetically altering the vaccine bacteria so as to change residues.

The motifs which are considered in creating such vaccines may be chosen on any of several grounds. If the pathogen to which the vaccine is directed is associated with an autoimmune disease, a motif may be developed according to the methods described herein for an HLA-DR protein associated with the disease. If there is also a known or suspected autoantigen, the motif may include TCR contact residues of the self epitope. The pathogens protein complement may then be compared to the motif and peptides corresponding to the motif may be omitted from the vaccine or may be altered by recombinant means to produce a vaccine free of such peptides. Alternatively, vaccines may be developed with particular populations in mind. For individuals suffering from or at risk of developing a particular autoimmune disease, special vaccines may be developed. In this case, the motif is again chosen on the basis of the HLA-DR protein associated with the autoimmune disease and, when known, the TCR contact residues of the self epitope.

In particular embodiments, such vaccine preparations are provided in which the HLA-DR protein is HLA-DR4 protein and the autoimmune disease is pemphigus vulgaris. And, in particular, vaccines are provided lacking a peptide corresponding to the PV motif #1 disclosed herein. Specific embodiments of the vaccines include vaccines lacking at least one of the peptides disclosed as SEQ ID NO.: 1 through SEQ ID NO.: 7. Thus, methods of immunizing an individual against pathogens which may cause pemphigus vulgaris are also provided.

Similarly, vaccine preparations are provided in which the HLA-DR protein is HLA-DR2 protein and the autoimmune disease is multiple sclerosis. And, in particular, vaccines lacking a peptide corresponding to at least one of the three MS motifs disclosed herein are provided. Specific embodiments of the vaccines include vaccines lacking at least one of the peptides disclosed as SEQ ID NO.: 8 through SEQ ID NO.: 15. In particularly preferred embodiments, the vaccines are developed from the pathogens listed in Table 2 but lack either the entire protein listed as the antigen or lack at least the peptides identified in the corresponding sequences. Thus, methods of immunizing an individual against pathogens which may cause multiple sclerosis are also provided.

These peptides will also be useful in assessing which pathogen(s) may be important in a particular patient. For example, the T cells from one patient may proliferate in response to one or a few of these peptides, while those from another patient may proliferate in response to a different peptide or set of peptides. Analogs of the peptides may be synthesized in which one of the T cell receptor contact residues is substituted. For example, in the case of MS, peptides with the substitution of MBP91F by 91A or of MBP93K by 93A may be employed. Such analogs are not, however, limited to the substitution of these primary T cell receptor contact residues of to substitution by particular amino acids such as A. These peptide analogs may be used to anergize (inactive) autoreactive T cells (see, for example, Sloan-Lancaster et al., 1993 and 1994) upon administration to autoimmune patients. The viruses or bacterial pathogens may be useful in immunization by selecting viral or bacterial strains that do not carry the mimicry epitope. Proteins from these pathogens other than those that carry the mimicry epitope may also be selected for immunization. This therapy may be useful in preventing reinfection and thus remissions of the disease or in preventing initial infections in particularly susceptible populations (the most obvious example of which is a disease-free identical twin of a patient).

EXAMPLES

1. Identification of Self Epitopes of Pemphigus Vulgaris

As noted above, pemphigus vulgaris (PV) is, in different ethnic groups, associated either with a DR4 allele (DRB1*0402) or with a rare DQ1 allele (DQB1*05032); only a small fraction of PV patients have neither susceptibility gene (Ahmed et al., 1991; Ahmed et al., 1990; Scharf et al., 1988b). The PV associated molecule has a negative charge (Glu) at the critical position β71; the neighboring position (β70) is also negatively charged. The DR4 subtype associated with PV is the only one that carries a negative charge at DRβ 71 (a positive charge (Arg) is found at DRβ71 in the RA associated DR4 molecules). Although polymorphic, the P7 pocket residue DRβ 67 (Leu/Ile) does not appear to be involved in peptide binding but probably acts as a TCR contact residue (Stern et al., 1994).

The charge of a polymorphic residue at DRβ 71 could therefore account for susceptibility to two different autoimmune syndromes associated with structurally similar DR4 subtypes: DR4 alleles associated with susceptibility to rheumatoid arthritis have a positive charge at DRβ 71 (Arg) while the DR4 allele associated with pemphigus vulgaris has a negative charge at DRβ 71 (Glu). Peptides selective for either DR4 molecule may therefore differ significantly in their charge at P4: Peptides with a negative charge at P4 would be expected to bind to the RA associated molecules but not the pemphigus associated DR4 molecule; in contrast a positive charge would be expected for the pemphigus peptide(s) at position 4. Due to the conserved nature of these molecules other peptide anchor residues (P1 and P6) would not be expected to be different for these DR4 subtypes.

A sequence motif for selective binding to the HLA-DR DRB1*0402 protein was developed according to the method disclosed herein.

The β chain residues involved in forming the P1 pocket for this allele are β85 (Val), β86 (Val), β89 (Phe) and β90 (Thr). Thus, the presence of Val at β86 (instead of Gly as in DRB1*0101) suggests that the P1 position of the motif be restricted to V, L, I, M and F. Alanine might also have been included but was not in this example. The P6 pocket is formed in part by the β11 (Val) and β13 (His) of the DRB1*0402 protein. Relative to the DRB1*0101 allele, in which these residues are Leu and Phe respectively, the P6 pocket of the DRB1*0402 protein is somewhat larger and more polar. Thus, for the P6 position of the motif, S, T, N and V were allowed. Finally, the P4 pocket of this DR protein is formed in part by the residues β13 (His), β70 (Asp), β71 (Glu), β74 (Ala) and β378 (Tyr). As rioted above, the two negatively charged residues as β70 and β871 create a preference for positively charged antigen residues and, therefore, the motif for the P4 position was restricted to K and R.

Thus, the sequence motif for the pemphigus vulgaris autoantigen was defined as:

| Position    | P1 | P2 | P3 | P4 | P5 | P6             |
|-------------|----|----|----|----|----|----------------|
| PVMotif #1: | V  | X  | X  | K  | X  | S (SEQ ID NO:21) |
|             | L  |    |    | R  |    | T              |
|             | I  |    |    |    |    | N              |
|             | M  |    |    |    |    | V              |
|             | F  |    |    |    |    |                |

Although the autoantigen for pemphigus vulgaris is known, the precise epitopes within the autoantigen have previously remained unknown. Using the method of the present invention, however, it has been possible to identify a small set of peptides which may serve as the autoantigenic determinants. The target antigen of pemphigus vulgaris is an epithelial adhesion molecule of the cadherin family, desmoglein 3 (Amagai et al., 1991). Desmoglein 3 mediates Ca$^{++}$ dependent adhesion between keratinocytes; the autoantibodies interfere with cell adhesion with resulting blister formation (Takeichi, 1990). The autoantibodies are thought to be pathogenic since a transient blistering disease is also seen in newborns of affected mothers due to transfer of maternal immunoglobulin to the fetus. Transfer of serum or desmoglein 3 specific antibodies to mice also results in acantholysis (Amagai et al., 1992).

Only seven peptides from this large protein (130 kDa, 999 amino acids) matched the motif. These seven pemphigus vulgaris antigens (PVA.1-PVA.7) are presented below in Table 1 with the residues corresponding to the MHC binding positions P1, P4 and P6 underlined.

TABLE 1

| PVA.1 (res. 78–93)   | ATQKITYRISGVGID (SEQ ID NO:1)   |
| PVA.2 (res. 97–111)  | FGIFVVDKNTGDINI (SEQ ID NO:2)   |
| PVA.3 (res. 190–204) | LNSKIAFKIVSQEPA (SEQ ID NO:3)   |
| PVA.4 (res. 206–220) | TPMFLLSRNTGEVRT (SEQ ID NO:4)   |
| PVA.5 (res. 251–265) | CECNIKVKDVNDNFP (SEQ ID NO:5)   |
| PVA.6 (res. 512–526) | SARTLNNRYTGPYTF (SEQ ID NO:6)   |
| PVA.7 (res. 762–786) | QSGTMRTRHSTGGTN (SEQ ID NO:7)   |

Therefore, the selective presentation of one or several of these peptides by the PV associated DRB1*0402 molecule to T cells may be critical for initiating autoimmunity in PV. To test this, T cell lines were raised from blood mononuclear cells of two patients with active disease by stimulation with the seven candidate peptides. T cell lines were expanded with rIL-2 and tested for recognition of the candidate peptides in a proliferation assay. T cell lines from both patients recognized two peptides from the extracellular domain of desmoglein 3 (PVA.3 and PVA.4) that were located close to the major autoantibody recognition site. These T cell lines were HLA-DR restricted as T cell proliferation was blocked by a monoclonal antibody specific for HLA-DR but not by a control antibody. These desmoglein 3 peptides are therefore candidates for the T cell dependent induction of autoimmunity in pemphigus vulgaris.

The motifs of the present invention relating to the. HLA-DR proteins can be taken one step further. In a different ethnic group PV is associated with a rare DQ1 subtype (DQB1*05032) that differs from the common DQ1 subtype only at position 57 of the DQβ chain (Sinha, et al., 1988). In the PV associated molecule DQβ 57 is negatively charged (Asp) whereas in the common DQ1 subtype it is not. The same position on the DQβ chain has also been implicated in susceptibility to diabetes. In diabetes, however, the reverse is true: DQ2 and DQ8 molecules associated with susceptibility to diabetes do not have a negative charge at DQβ 57 (Todd et al., 1987).

Based on these observations it becomes clear that two polymorphic positions in the MHC class II β chain (position 71 of DRβ and position 57 of DQβ) are critical for selective peptide binding and the development of autoimmunity. Based on the criteria described above, a diabetes linked peptide would be expected to have a negative charge at P9 since such a peptide would only bind to DQ molecules that do not have the same charge at DQβ 57. In contrast, for the DQ1 associated cases of pemphigus, a peptide with a positive charge at P9 may be selective for the disease associated molecule which carries a negative charge at DQβ 57. In the case of DR4 linked autoimmunity, the charge at peptide position 4 confers selectivity to the disease associated DR4 molecule: RA peptides have a negative charge at P4, PV peptides a positive charge at P4. Motifs for selective peptide binding may therefore prove to be tremendously useful in the identification of key epitopes that initiate human autoimmune diseases. This approach is expected to be useful not only for identifying peptides in PV, RA or diabetes but also for other autoimmune diseases where residues critical in peptide binding have been linked to disease susceptibility.

2. Identification of Mimics of the Multiple Sclerosis MBP Autoantigen

Susceptibility to MS is associated with HLA-DR2 (DRA, DRB1*1501, the most common subtype of DR2) (Spielman et al., 1982; Olerup et al., 1989). This MHC class II molecule is believed to play a critical role in the immunopathogenesis of MS by presenting immunodominant self peptides to autoreactive T cells. Following injection of MBP in experimental animals, T cells specific for immunodominant peptides of MBP mediate an inflammatory response in the CNS that can be accompanied by marked demyelination (reviewed in Zamvil and Steinman, 1990). In previous studies two regions of human MBP were found to be immunodominant (residues 84-102 and 143-168) (Ota et al. 1990; Pette et al. 1990; Martin et al. 1990; Wucherpfennig et al. 1994a). Reactivity to the MBP(84-102) peptide was predominantly seen in subjects carrying HLA-DR2. Using L cell transfectants as antigen presenting cells, HLA-DR2b (DRA, DRB1*1501) was found to serve as the restriction element for these MBP(84-102) specific T cell clones.

The MBP(84-102) peptide binds with high affinity to the HLA-DR2b molecule with two hydrophobic residues serving as the anchors P1 (Val 89 of MBP) and P4 (Phe 92 of MBP) (Wucherpfennig et al., 1994a; Vogt et al. 1994). At position P1, Val 89 can be substituted by other aliphatic amino acids (Leu, Ile), as well as by methionine and phenylalanine; alanine is tolerated at this position but reduces the affinity of the peptide for HLA-DR2b. At position P4, all aliphatic and aromatic residues are permitted; again alanine is tolerated but results in a loss of binding affinity.

A mutational analysis of putative TCR contact points confirms that P3 (Phe 91) and P5 (Lys 93) are TCR contacts for the MBP(85-99) specific clones; other residues such as P-1 (Val 88) and P2 (His 90) are important for some clones but not for others. Substitution of P3 (Phe 91) by alanine abolishes TCR recognition for all clones; some clones tolerated conservative substitutions (eg. tyrosine or aliphatic amino acids) while other clones do not. Substitution of P5 (Lys 93) by arginine is tolerated by most T cell clones but more drastic changes frequently result in a partial or complete loss of T cell reactivity. This analysis demonstrates that P2 (His 90), P3 (Phe 91) and P5 (Lys 93) are the primary TCR contact residues for MBP while P1 (Val 89) and P4 (Phe 92) are the primary MHC contact residues for MBP. This analysis also confirms the present teaching that the TCR contact residues of a motif should be highly if not absolutely conserved.

Based on this structural characterization of the immunodominant MBP(85-99) peptide, three sequence motifs were developed to search a protein database for viral and bacterial peptides that matched these requirements. The motifs focused on the core region of the peptide, residues P-1 to P5 (88-93 of the MBP protein), which contained the MHC and TCR contacts common to all clones. In the first motif, aliphatic amino acids were allowed at the first MHC anchor residue P1 while both aliphatic and aromatic residues were permitted at the second MHC anchor P4. For the TCR contacts, the Phe 91 at P3 was absolutely conserved, the Lys 93 at P5 could be substituted only by arginine, while the His 90 at P2 and the Val 88 at P-1 could be substituted by several structurally related amino acids. Thus, the first motif for multiple sclerosis antigens was defined as:

| Position | P-1 | P1 | P2 | P3 | P4 | P5 |
|---|---|---|---|---|---|---|
| MS Motif #1: | V | V | H | F | F | K (SEQ ID NO:18) |
| | L | L | N | | Y | R |
| | I | I | Q | | W | |
| | A | A | F | | V | |
| | M | M | | | L | |
| | | | | | I | |
| | | | | | A | |
| | | | | | M | |

The second motif omitted the Val 88 P-1 as a TCR contact residue (used only by some clones) and permitted also aromatic amino acids at the first MHC anchor P1 (Val 89). This was done since the MBP(85-99) peptide is presented by different HLA-DR2 subtypes: Presentation by DRB1*1501 requires an aliphatic amino acid or phenylalanine at this position while aliphatic and all aromatic residues at this position can serve as anchor for DRB1*1602. This difference, as explained above, relates to the size of the primary pocket for binding this hydrophobic residue and is determined by the Val/Gly dimorphism at DR386 (Val in *1501 and Gly in *1602) (Busch et al., 1991). Thus, the second motif for multiple sclerosis antigens was defined as:

| Position    | P1 | P2 | P3 | P4 | P5             |
|-------------|----|----|----|----|----------------|
| MS Motif #2:| F  | H  | F  | F  | K (SEQ ID NO:19)|
|             | Y  | N  |    | Y  | R              |
|             | W  | Q  |    | W  |                |
|             | V  | F  |    | V  |                |
|             | L  |    |    | L  |                |
|             | I  |    |    | I  |                |
|             | A  |    |    | A  |                |
|             | M  |    |    | M  |                |

The third sequence motif represented a modification of the TCR contact residues preferred by a subgroup of MBP (85-99) specific clones. For these clones, P5 (Lys 93) was absolutely conserved while P3 (Phe 91) could be substituted by some aromatic or aliphatic amino acids. The third motif for multiple sclerosis antigens was defined as:

| Position    | P1 | P2 | P3 | P4 | P5             |
|-------------|----|----|----|----|----------------|
| MS Motif #3:| V  | H  | F  | F  | K (SEQ ID NO:20)|
|             | L  | F  | Y  | Y  |                |
|             | I  | Y  | W  | W  |                |
|             | A  | W  | V  | V  |                |
|             | M  |    | L  | L  |                |
|             |    |    | I  | I  |                |

These HLA-DR motifs also matched well with the structural requirements for an HLA-DQ1 restricted clone specific for the MBP(85-99) peptide. This clone required the same minimal peptide segment as DR2 restricted clones (residues 87-97). As in the DR2 restricted clones, P2 (His 90), P3 (Phe 91) and P5 (Lys 93) appeared to be the primary TCR contact residues. Substitution of these hydrophobic positions by aspartic acid greatly diminished the stimulatory capacity of the peptide while substitutions by other hydrophobic amino acids were tolerated. These data suggest that the MBP(85-99) peptide is bound in a similar fashion to HLA-DR2b and to HLA-DQ1 and that the same peptide residues are critical for interaction with the TCR.

These motifs were used as search criteria in a search of protein databases (PIR and SwissProt) using the Genetics Computer Group software (program: findpatterns). More than 600 sequences of viral and bacterial origin were identified that matched these criteria. From this set, sequences were selected based on the following criteria: (1) Viruses known to cause human pathology, (2) Viruses prevalent in the Northern Hemisphere where MS occurs most frequently, (3) Selected bacterial sequences associated with inflammatory CNS disease (such as *Borrelia burgdorferi*) and with invasive infections (such as *Staphylococcus aureus, Klebsiella pneumoniae* and *Pseudomonas aeruginosa*). Not included were most viruses that cause infections in tropical countries, sequences derived from vaccinia virus and a large number of sequences from *E. coli* (which is part of the normal intestinal flora). When multiple antigenic variants were present, one or several sequences that best fit the motifs were chosen. The selected peptides were synthesized by Pin-Technology on a 1 mg scale (Chiron Mimotopes, San Diego). Seventy peptides were made which fit motifs #1 and #2 and 59 peptides for motif #3.

These peptides were then tested for their ability to activate human MBP(85-99) specific T cell clones that had been previously established from blood T cells of two patients with relapsing-remitting MS (Wucherpfennig et al., 1994a; Wucherpfennig et al., 1994b). Homozygous B cell lines that expressed DR2 (DRB1*1501 or DRB1*1602) or DQ1 were used as antigen presenting cells (APCs) in these T cell proliferation experiments (Wucherpfennig et al., 1994a). As a positive control, all clones were shown to be activated by/the MBP(85-99) peptide. Seven clones were tested with the viral/bacterial peptides selected according to the sequence motifs.

Three of the seven clones tested were efficiently activated by several viral/bacterial peptides. The first clone (Hy.1B11) was HLA-DQ1 restricted whereas the other two clones (Hy.2E11 and Hy.1G11) were HLA-DR2 restricted (Wucherpfennig et al., 1994a). Among the 70 peptides selected according to motifs #1 and #2, three mimicry peptides stimulated the DQ1 restricted clone and two peptides stimulated both of the DR2 restricted T cell clones. Among the group of 59 peptides selected according to motif #3, one peptide was identified for the DQ1 restricted clone while two were identified for the DR2 restricted clones.

Taken together, the DQ1 restricted T cell clone recognized five structurally related peptides: the immunodominant MBP(85-99) peptide, three viral peptides (from Herpes simplex, Adenovirus type 12 and Human Papillomavirus) and a bacterial peptide (*Pseudomonas aeruginosa*). Two of the DR2 restricted clones were activated by four peptides. Both clones recognized the MBP(85-99) peptide as well as peptides from EBV and Influenza virus. In addition, one clone recognized a viral peptide from Reovirus (clone Hy.2E11) and one recognized a peptide from Herpes simplex virus (clone Hy.1G11). These results, and the sequences of these peptides, are summarized below in Table 2.

TABLE 2

Peptides Recognized by Clone Hy.1B11 (DQ1 Restricted):

| | |
|---|---|
| MBP(85–99) | ENPVVHFFKNIVTPR (SEQ ID NO:16) |
| Herpes Simplex, UL15 Protein | FRQLVHFVRDFAQLL (SEQ ID NO:8) |
| Adenovirus Type 12, ORF | DFEVVTFLKDVLPEF (SEQ ID NO:9) |
| *Pseudomonas aeruginosa*, Phosphomannomutase | DRLLMLFAKDVVSRN (SEQ ID NO:10) |
| Human Papillomavirus Type 7, L2 Protein | IGGRVHFFKDISPIA (SEQ ID NO:11) |

Peptides Recognized by Clone Hy.2E11 (DR2 Restricted):

| | |
|---|---|
| MBP(85–99) | ENPVVHFFKNIVTPR (SEQ ID NO:16) |
| Epstein-Barr Virus, DNA Polymerase | TGGVYHFVKKHVHES (SEQ ID NO:12) |
| Influenza Type A, Hemagglutinin | YRNLVWFIKKNTRYP (SEQ ID NO:13) |
| Reovirus Type 3, Sigma 2 Protein | MARAAFLFKTVGFGG (SEQ ID NO:14) |

Peptides Recognized by Clone Hy.1G11 (DR2 Restricted):

| | |
|---|---|
| MBP(85–99) | ENPVVHFFKNIVTPR (SEQ ID NO:16) |
| Epstein-Barr Virus, DNA polymerase | TGGVYHFVKKHVHES (SEQ ID NO:12) |
| Influenza Type A, Hemagglutinin | YRNLVWFIKKNTRYP (SEQ ID NO:13) |
| Herpes Simplex, DNA Polymerase | GGRRLFFVKAHVRES (SEQ ID NO:15) |

For these viral/bacterial peptides to be involved in the initiation of autoimmunity, they have to be capable of potent T cell stimulation that results in marked clonal expansion of autoaggressive T cell clones. The stimulatory capacity of each of these peptides was therefore compared to the MBP (85-99) peptide in a titration experiment. The peptides were found to be efficient stimulators of the MBP specific T cell clones; in particular the EBV peptide (DR2 restricted clones) and the adenovirus peptide (DQ1 restricted clone) were similar to the MBP(85-99) peptide in their stimulatory capacity. These results demonstrate that the T cell activation is not the result of a minor degree of 'cross-reactivity' but rather the result of structural similarity sufficient for potent T cell activation.

Comparison of the peptide sequences that were found to stimulate the same TCR revealed several interesting points:

(1) only one peptide (Human Papillomavirus L2 protein) had striking sequence similarity with the MBP(85-99) peptide in that all amino acids in the MBP(89-95) segment except position 94 (Asn to Asp) were identical (Table 2). For all other sequences, simple alignment would not have predicted them to be efficient stimulators of MBP(85-99) specific T cell clones. Therefore, absent the method of the present invention, these peptides would not have been identified.

(2) At positions not specified by the search criteria, the selection for particular amino acids was still apparent (Table 2). For the DQ1 restricted clone, for example, aspartic acid was selected at position P6 (residue 94 of MBP), a probable TCR contact residue, in all four peptides. This position is occupied by asparagine in the MBP peptide (similar size, but no negative charge). Substitution of Asn 94 for Asp in the MBP peptide markedly increased its stimulatory capacity for the DQ1 restricted clone but reduced it for the DR2 restricted clone. Selection also occurred at the neighboring P7 MHC contact (Ile 95) for which Ile, Val or Phe were selected (all hydrophobic).

(3) Different selection events occurred for the DQ1 and the DR2 restricted clones: At position P6 (94 of MBP), there was selection of aspartic acid (negative charge) for DQ1 peptides whereas there was selection for lysine (positive charge) in two of the three peptides presented by DR2.

(4) In the flanking segments (residues 85-87 and 97-99), no apparent selection took place as amino acids with different size and charge were allowed.

The majority of the viruses from which these sequence peptides were identified are common human pathogens: Influenza Type A frequently causes respiratory tract infections; Human Papillomavirus infects epithelial tissues and has been linked to cervical carcinomas; and Epstein-Barr Virus (EBV) causes an acute viral syndrome (infectious mononucleosis) in young adults. Human Herpesvirus I (Herpes simplex), EBV and Human Papillomavirus cause latent or persistent infections with neurons (Herpes simplex), B cells (EBV) and epithelial cells (Papillomavirus) serving as the reservoirs. Viral expression can be reactivated by UV exposure and stress (Herpes simplex) and by B cell activation (EBV) (Schwarz et al, 1985; Epstein et al., 1977; Spruance 1985; Tovey et al., 1978). For the induction and maintenance of an autoimmune response these persistent viral infections are of particular interest as they could explain the chronicity of the clinical disease and the clonal expansion and persistence of MBP specific T cells. Reactivation of viral expression may also be involved in triggering clinical relapses. By this mechanism, viral peptides could activate resting MBP specific T cells in periphery and allow them to invade the CNS.

Are these foreign epitopes actually presented to autoreactive T cells during a viral infection? The peptide from the EBV DNA polymerase allowed this question to be addressed. In EBV transformed B cells (which were used as antigen presenting cells in the T cell assays) the lytic viral cycle is repressed. The DNA polymerase gene is not transcribed in this latent state; however, B cell activation results in activation of the lytic cycle and in the expression of the DNA polymerase gene (Datta et al., 1980). To examine MHC class II restricted presentation of the EBV DNA polymerase, an HLA-DR2$^+$ EBV transformed B cell line (MGAR) and an MHC mismatched control (9001, HLA-DR1) were pretreated for 36 hours with phorbol ester which was removed by extensive washing prior to coculture of APC with T cells. T cell clones Hy.2E11 and Hy.1G11, which recognize the EBV DNA polymerase peptide presented by HLA-DR2, were activated by a HLA-DR2$^+$ EBV transformed B cell line pretreated with phorbol ester. This effect was specific because MHC mismatched B cells did not activate the clones; also, a control clone (Ob.1A12) that recognized MBP(85-99) but not the EBV peptide was not activated. In a separate experiment, T cell activation was blocked by a mAb specific for HLA-DR (mAb L243) but not by a mAb specific for HLA-DQ (G2a.5). These results demonstrate that the MBP specific T cell clones recognize not only the viral peptide but also antigen presenting cells infected with the virus. In vivo this recognition event could lead to chronic antigenic stimulation of MBP specific T cells as B cell activation results in the expression of EBV genes, including the DNA polymerase gene.

Finally, the presentation of the viral peptides by different DR2 subtypes was compared to determine if they are efficiently presented by the disease associated molecule (DRB1*1501, the most common DR2 subtype). The MBP peptide was presented by three of the four DR2 subtypes; the peptide was not presented by DRB1*1601 which differs from DRB1*1602 by a single amino acid substitution (at position DRB67, a possible TCR contact). The two viral peptides were presented much better by the DR15 molecules (DRB1*1501 and 1502 which differ only at position DRB86) than by DRB1*1602. This was particularly evident for the influenza peptide which only activated the T cell clone when presented by the DRB1*1501/1502 molecules but not by DRB1*1602. These results indicate that the viral peptides identified herein are preferentially presented by the MS associated DR2 molecule (DRB1*1501).

DEFINITIONS

For clarity of interpretation and to clearly and distinctly point out the subject matter of the claimed invention, the following definitions are provided for several terms used in the claims appended hereto.

The term "sequence motif," in accordance with description provided herein, means a series of restrictions on the residues which may occupy certain relative positions of an amino acid sequence. A sequence motif must restrict at least three and preferably four or five positions of an amino acid sequence. The relative positions of the first (N-terminal) and last (C-terminal) restricted amino acid positions shall be separated by at least two but no more than twelve amino acid residues. For example, P1 and P4 may be the first and last restricted residues and these residues are separated by two residues. As another example, P-1 and P11 may be the first and last restricted residues and these are separated by ten residues. Positions between the first and last restricted positions may be restricted or unrestricted with the exception that a total of at least three positions of the motif must be restricted. Of the three positions which must be restricted, at least two must be residues corresponding to major MHC binding pockets. If only two of the restricted residues correspond to MHC binding residues, the third must correspond to a TCR contact residue. Further, at least one of the positions restricted must correspond to either the P1 or P4 binding position. By "restricted" is meant that at least one, and preferably ten, amino acid residues shall be excluded from a position.

An amino acid sequence "corresponds" to a sequence motif if it can be aligned with the positions of the sequence motif such that, at each restricted position of the motif, the amino acid sequence includes a residue which is not excluded from that position by the restrictions which define the motif. As the restrictions which define the motif are derived from the size and nature of the MHC binding pockets of HLA-DR proteins and, optionally, the TCR contact residues of known epitopes, the restricted positions of the binding motif may also be said to correspond to the MHC binding pockets and TCR contact residues.

The term "isolated," in reference to a protein or polypeptide, means separated from its native or natural chemical microenvironment. Thus, a polypeptide isolated from a bacterium shall be in a preparation substantially free of most of the other bacterial polypeptides and, similarly, an isolated viral polypeptide preparation shall be substantially free of the other polypeptides which comprise the virus.

The term "associated with," as used in connection with a particular HLA-DR protein and an autoimmune disease or autoimmune response, shall mean that the protein and the disease/response have been positively correlated by clinical or epidemiological studies such that the likelihood of developing the disease/response has been shown to be increased by presence of the protein.

The term "HLA-DR protein" means the particular protein product of a particular allele of the MHC class II HLA-DR gene. A disease associated with an HLA-DR protein is one associated with such a particular protein and not merely with the HLA-DR gene locus.

By the term "human pathogen" is meant a bacterium, virus or protozoon capable of infecting humans and generating an immune response. The term specifically is intended to exclude the bacteria which form part of the normal human intestinal flora. By this term, "normal human intestinal flora," is meant the bacteria which normally inhabit the human gut, such as *Escherichia coli*, but which do not normally cause disease.

By the term "autoreactive," as applied to T cells, is meant T cells from a human which are activated by a human self epitope. By "activation" of T cells is meant induction to proliferate, secrete lymphokines (cytokines) and/or to initiate effector activity (e.g. cytotoxicity).

By the term "autoantigen" is meant a self protein or polypeptide which includes a "self epitope." By "self epitope" is meant that part of an autoantigen which is recognized by T cells when bound to and presented by an MHC molecule.

By the term "effective amount," with respect to tolerizing an individual to an antigen, is meant an amount of the antigen sufficient to render T cells, otherwise specific for the antigen, unresponsive to the antigen when bound to and presented by an MHC molecule. T cells which are unresponsive fail to activate when presented with the antigen for which they are specific. By the term "effective amount," with respect to immunizing an individual to an antigen, is meant an amount sufficient to induce an immune response which results in T cells specific for the antigen. Typical ranges of dosages are from 1 nanogram/kilogram to 100 milligrams/kilogram or even 500 milligrams/kilogram. Effective amounts will vary according to such factors as age sex and sensitivity to the antigen.

By the term "core MHC binding residues" is meant the residues of an epitope corresponding to the P-1 to P9 positions of a peptide bound to an HLA-DR molecule. By the term "inner core MHC binding residues" is meant those residues of an epitope corresponding to the P-1 to P6 positions of a peptide bound to an HLA-DR molecule.

We claim:

1. A composition comprising (i) a pharmaceutically acceptable carrier; and (ii) an isolated polypeptide consisting of the amino acid sequence set forth in SEQ ID NO: 1, SEQ ID NO: 2, SEQ ID NO: 3, SEQ ID NO: 4, SEQ ID NO: 5, SEQ ID NO: 6, or SEQ ID NO: 7.

2. The composition of claim 1, wherein said polypeptide consists of the amino acid sequence set forth in SEQ ID NO: 3, SEQ ID NO: 4, SEQ ID NO: 5, or SEQ ID NO: 7.

* * * * *

UNITED STATES PATENT AND TRADEMARK OFFICE
CERTIFICATE OF CORRECTION

| | |
|---|---|
| PATENT NO. | : 7,255,861 B1 |
| APPLICATION NO. | : 08/991628 |
| DATED | : August 14, 2007 |
| INVENTOR(S) | : Jack L. Strominger et al. |

It is certified that error appears in the above-identified patent and that said Letters Patent is hereby corrected as shown below:

In the Specification

At Column 1, Line number 12, please add the following:
GOVERNMENT FUNDING
This invention was made with government support under CA047554 awarded by the National Institutes of Health. The government has certain rights in the invention.

Signed and Sealed this
Tenth Day of December, 2024

Katherine Kelly Vidal
*Director of the United States Patent and Trademark Office*